United States Patent
Georg et al.

(10) Patent No.: US 6,410,051 B1
(45) Date of Patent: Jun. 25, 2002

(54) COMPRESSED CHLORAMINE-T TABLETS AND METHOD FOR THE PRODUCTION THEREOF

(75) Inventors: Rolf Georg; Hartmut Bosch, both of Ammerbuch (DE)

(73) Assignee: RMP chemisch-technische Spezialprodukte GmbH and Co. KG, Ammerbuch (DE)

( * ) Notice: Subject to any disclaimer, the term of this patent is extended or adjusted under 35 U.S.C. 154(b) by 0 days.

(21) Appl. No.: 09/486,793

(22) PCT Filed: Aug. 28, 1998

(86) PCT No.: PCT/EP98/05466
§ 371 (c)(1),
(2), (4) Date: May 11, 2000

(87) PCT Pub. No.: WO99/11126
PCT Pub. Date: Mar. 11, 1999

(30) Foreign Application Priority Data

Sep. 3, 1997 (DE) .......................... 197 38 424
Dec. 12, 1997 (DE) .......................... 197 55 258

(51) Int. Cl.⁷ .............................. A61K 9/20; A61K 9/14
(52) U.S. Cl. .................. 424/464; 424/488; 424/484; 424/486
(58) Field of Search ............... 424/464, 94.63, 424/94.64, 488, 484, 486

(56) References Cited

U.S. PATENT DOCUMENTS 5,985,629 A * 11/1999 Aaslyng et al. ............. 435/174

FOREIGN PATENT DOCUMENTS

| DE | 1808253 | 6/1970 |
| DE | 2835683 | 2/1979 |
| DE | 3913391 | 10/1990 |
| GB | 955897 | 5/1964 |
| GB | 1131998 | 10/1968 |

OTHER PUBLICATIONS

Martindale: The Extra Pharmacopoeia, twenty–ninth edition, p 955.*
Chemical abstracts, vol. 101, No. 2, Jul. 9, 1984, Columbus, Ohio, US; abstract No. 12137, V. Andonova et al.: "Stabilization of Chloramine B in Tablet Forms", XP002090784 (see abstract and Farmatsiya, vol. 33, No. 6, 1983, pp. 34–37.

* cited by examiner

Primary Examiner—Thurman K. Page
Assistant Examiner—Blessing Fubara
(74) Attorney, Agent, or Firm—Baker Botts L.L.P.

(57) ABSTRACT

The invention relates to compressed tablets containing more than 50 wt. % chloramine-T as the main constituent, as well as at least one pressing agent and at least one agent aiding rapid dissolving as secondary constituents, as well as a method for the production thereof.

24 Claims, No Drawings

COMPRESSED CHLORAMINE-T TABLETS AND METHOD FOR THE PRODUCTION THEREOF

The invention relates to pressed or compressed chloramine-T tablets and a method for the production thereof. Chloramine-T is a known disinfecting and antistaling agent, which is usable in wide ranges of application. It is normally in the pulverulent state, where it is difficult to handle. This is in part due to the fact that the powder easily flies up during handling. It is therefore desirable to have chloramine-T in a compact form, particularly in a tablet form. Tablets containing chloramine-T are already known. These tablets are used for keeping cut flowers fresh, in that they are added to the water for the flowers. However, the tablets have an active ingredient content below 20 wt. %.

For the industrial use of chloramine-T, particularly in the hygiene sector, food production and disinfection, not only are larger chloramine-T quantities necessary, but also higher chloramine-T active ingredient contents are desired, namely for cost reasons, transportation reasons and for avoiding larger quantities of auxiliary agents or adjuvants, which have no effect and are prejudicial during use or can give rise to disposal problems. However, without larger quantities of pressing or compressing agents, it is not possible to press or compress pulverulent chloramine-T with an adequate strength.

The problem of the invention is therefore to provide chloramine-T tablets with a high active ingredient content and correspondingly low quantities of pressing agents and other additives. The tablets are to have an adequate strength for handling, associated with a rapid dissolvability.

The compressed tablets according to the invention contain more than 50 wt. % of chloramine-T as the main constituent, as well as at least one pressing agent and at least one agent aiding rapid dissolving, particularly a disintegrating agent, as secondary constituents. Apart from pressing agents and solubilizers or disintegrating agents, if desired, further secondary constituents may be present, particularly fillers or also other adjuvants or auxiliary agents, such as antifoaming agents. The chloramine-T active ingredient content is preferably at least 80 wt. %, particularly at least 90 wt. %. In special cases it can even be up to 97 wt. %. Such high active ingredient contents are made possible through the combination of pressing agents and solubilizers.

Preferably at least one of the secondary constituents has combined characteristics and serves both as a pressing agent and as a solubilizer. In this way it is possible to keep the content of secondary constituents low and to correspondingly raise the active ingredient content. As pressing agents are in particular suitable magnesium stearate, highly disperse amorphous silica (silicon dioxide), pulverulent polyethylene glycols, sodium carboxymethyl cellulose and/or microcrystalline cellulose.

As agents aiding rapid dissolving, particularly as disintegrating agents, are in particular suitable sodium carboxymethyl starch or sodium-starch-glycolate, prepasted corn starch, sodium carboxymethyl cellulose and/or pulverulent polyethylene glycols. These constituents are more particularly suitable because even in small proportional quantities of 0.25 to less than 5 wt. %, particularly in combination with one another, they evolve their full efficacy. The mixture preferably contains at least approximately 60%, particularly at least approximately 80% of the aforementioned substances.

Chloramine-T ((N-chloro-p-toluenesulphonamido) sodium) has a very broad action spectrum as a disinfectant. It is active against bacteria, viruses, yeasts, fungi and algae, so that there is a very wide application spectrum. Great significance is attached here to the hygiene sector, particularly in clinics, public baths abattoirs, etc. It is a valuable disinfectant in agriculture and in veterinary medicine. It is suitable for conserving water, particularly for keeping fountains clean. According to the invention the tablets have an active ingredient content of chloramine-T of more than 50 wt. %. In fact, higher active ingredient percentages are possible and desired. Thus, as a rule, the active ingredient proportion is at least 70 wt. % or higher. Tablets with a high chloramine-T content have an active ingredient content of 80 or 90 wt. %. The weight proportion of auxiliary substances is correspondingly low and substantially and generally make up the difference to 100%. However, it has been found that a larger number of auxiliary substances, which exercise a mutual, synergistic effect, is more favourable than a higher weight proportion of only a few auxiliary substances.

Preferred embodiments contain as auxiliary substances or secondary constituents several or most of the following substances:

a) Highly disperse amorphous silicon dioxide (silica). This is used as a pressing aid and lubricant. It is generally present in quantities of 0.25 to 2 wt. %, particularly 0.5 to 1 wt. %.

b) Sodium carboxymethyl cellulose. This can be present in the form of different types, particularly with a degree of substitution of 0.75 to 0.8. Sodium carboxymethyl cellulose acts both as a binder and as a solubilizer (disintegrating agent). It is generally present in quantities of 1 to 3 wt. %, particularly 1.5 to 2 wt. %.

c) Sodium carboxymethyl starch and/or sodium-starch-glycolate. The latter is in particular an excellent disintegrating agent. The quantities are generally 0.5 to 4 wt. %, particularly 1 to 2.5 wt. %. Croscarmellose (AVEBE) is also suitable as a disintegrating agent.

d) Corn starch, particularly prepasted corn starch. The latter serves as a disintegrating agent and cooperates in an excellent manner with sodium carboxymethyl starch and in particular sodium-starch-glycolate. The quantities are generally 0.5 to 10 wt. %, particularly 1 to 3 wt. %.

e) High purity microcrystalline cellulose. The latter has the function of a filler or binder and aids a homogeneous mixing during the mixing of the individual constituents. The quantities are generally 0.5 to 10 wt. %, particularly 1 to 3 wt. %.

f) Polyethylene glycols. These are generally present in the mixture as pulverulent solids. They have binder characteristics for the tablet, but also aid dissolving. The quantities are generally 1 to 5 wt. %, particularly 2 to 3 wt. %.

g) Gum Arabic. The latter serves as a binder and can in particular also be used in place of polyethylene glycols. The quantities are generally 0.5 to 5 wt. %, particularly 1 to 3 wt. %.

h) Magnesium stearate. This is a known pressing agent, which allows the tablet to have smooth surfaces and serves as a lubricant for the punch.

i) Sodium chloride (common salt). This is used for the electrochemical stabilization of chloramine-T at higher temperatures and under non-optimum storage conditions. The quantities are generally 1 to 5 wt. %, particularly 2 to 3 wt. %.

Apart from these constituents, for special application purposes further constituents can be present, such as e.g.

antifoaming agents in water treatment and the like. Surfactants or detergents, together with dyes and perfumes can also be present. Stabilizing agents can also be used for ensuring storage stability and activity under extreme environmental conditions. These further constituents for special applications are added to the 100% of the aforementioned constituents. Surfactants can be present in quantities of 0.5 to 30 wt. %, particularly 0.5 to 2 wt. %, stabilizers in quantities of 0.5 to 20 wt. %, particularly 0.5 to 3 wt. %, dyes or perfumes in quantities of 0.5 to 20 wt. %, particularly 0.5 to 2 wt. % additionally to the 100%. Approximately 1 to 5 wt. % are sufficient for antifoaming agents. Generally the total quantity of the further constituents together is less than 10 wt. %. If the further constituents also have characteristics as pressing agents or solubilizers, the quantity of the aforementioned pressing agents and solubilizers can be reduced. The individual constituents can also be replaced by others having an equivalent action.

In particularly preferred embodiments of the invention there are at least 4, particularly at least 6 of the aforementioned auxiliary substances present as secondary constituents in the tablet. The secondary constituents are either water-soluble, which is preferred, or are present in such a finely divided form or are obtained in such a finely divided form when the tablets disintegrate, that the complete tablet substantially forms a clear solution. Chloramine-T is in any case adequately water-soluble.

In a preferred embodiment the tablets are constructed as dosing tablets. For this purpose the tablet size is preferably adjusted in such a way that with predetermined, easily measurable liquid volumes it is possible to obtain solutions with a predetermined chloramine-T concentration. Chloramine-T is active in concentrations of 0.001 to 15 wt. % and normally solutions with a concentration of 5% or less are adequate. Preferably use is made of solutions with a chloramine-T active ingredient content of approximately 0.5 wt. %. Preference is therefore given to tablet sizes or dosing tablets with which in simple manner such active ingredient solutions can be prepared. For practical handling for example two tablet sizes are adequate, particularly one tablet size with an active ingredient content of 2.5 g of chloramine-T. If this tablet is dissolved in half litre of water, then an active ingredient solution is obtained with 0.5 wt. % chloramine-T. The other tablet size contains 50 g of chloramine-T. When dissolved in 10 litres of water once again active ingredient solutions of 0.5 wt. % chloramine-T are obtained. Larger tablets, particularly with a diameter of 20 mm or more are generally called tabs. The term tablets also covers larger pressed or compressed articles. Generally they have a cylindrical, particularly a flat cylindrical shape. However, the tablets can also have some other geometrical shape, e.g. a cubic or spherical construction. Preference is given to tablet shapes with a maximum large surface/weight, because this makes it possible to achieve very rapid dissolving rates. The tablet hardness is preferably so adjusted through the choice of the auxiliary agents and pressing conditions, that the tablets can still be broken by hand and as a result the rapid dissolving is also assisted. During pressing or compressing, it is also possible to impress preset breaking points. Even with larger tablets dissolving is possible within a period of less than one minute, particularly less than 45 seconds, dissolving preferably taking place accompanied by stirring. Dissolving can be carried out at ambient temperature. Heating is not necessary.

Chloramine-T is biogradable. Preferably the secondary constituents are selected in such a way that all the constituents are at least biologically unobjectionable. In particular, at least the main quantity of the secondary constituents is biogradable or compostable. This is the case with the aforementioned constituents. Particularly when used in hygiene and medicine, as well as for drinking water treatment, all the constituents should be present at least in DAB-10 quality, i.e. having the purity intended for pharmaceuticals. The tablets according to the invention advantageously have a smooth, closed surface, without being provided with a coating. This permits dustless handling. The density of the tablets is preferably in the range 1.0 to 1.3 $g/cm^3$ and in particular at approximately 1.1 $g/cm^3$. The tablets can have a per se known impression, which, in particular gives details on the active ingredient, the active ingredient quantity and/or the liquid volume used. It is also possible to impress a trademark. The impressions can be combined with the aforementioned preset breaking markings.

Preferably the tablets are placed in a pack, where the tablets are individually packed. This pack is in particular moisture-tight and airtight. As a result the tablets can be stored for a very long time and are insensitive to external influences. Soda kraft paper, which has a PE (polyethylene) coating is particularly suitable for packing purposes. This coating serves as a moisture barrier and simultaneously as a heat seal coating during packing. This coating is so thin that, following removal of the tablet, the packing is completely biodegradable, so that no special disposal is required.

The invention also relates to a method for producing the tablets according to the invention. In this method all the starting substances are premixed dry in pulverulent form, particularly in a very finely powdered form. The mixture is filled into a tablet press and compressed to tablets. Intermediate storage can take place between mixing and compression, because demixing need not be feared. Pressing can take place at pressures of 50 to 300 $N/mm^2$, particularly at 100 to 250 $N/mm^2$. For a tablet with an active ingredient content of 2.5 g of chloramine-T and a diameter of 20 mm this corresponds to a pressing pressure of 4 to 8 t and with a tablet having 50 g of solids and a diameter of 50 mm this corresponds to a pressing pressure of approximately 20 t up to 24 t. At these pressures tablets with a strength adequate for handling are obtained, but which, if desired, can still be broken with the hand.

Further features of the invention can be gathered from the following description of examples in conjunction with the subclaims. The individual features can be implemented individually or as a plurality combined together.

EXAMPLE 1

The following constituents are used in pulverulent form with a degree of purity of DAB 10.

90 parts by weight chloramine-T ((N-chloro-p-toluenesulphonamido) sodium)

0.5 parts by weight highly disperse amorphous silicon dioxide (silica)

2 parts by weight sodium carboxymethyl cellulose (high purity, degree of substitution 0.76)

1 part by weight sodium-starch-glycolate and/or sodium-croscarmellose 1 part by weight prepasted corn starch 2.25 parts by weight high purity, microcrystalline cellulose 3.0 parts by weight polyethylene glycols (pulverulent)

0.250 parts by weight magnesium stearate.

The powders are mixed dry in a gyrowheel mixer and supplied for intermediate storage in a hopper. The powder mixture has a density of approximately 0.8 g/cm. The desired powder quantity is removed from the hopper and pressed to dosing tablets with a predetermined active ingredient content. Two tablet sizes are provided, namely a tablet with a 20 mm diameter containing 2.5 g of chloramine-T (total weight 2.78 g) and a tablet with a diameter of 50 mm containing 50 g of chloramine-T (total weight 55.6 g). The pressed tablets or tabs are packed airtight by heat sealing in PE-coated soda kraft paper. For preparing a 0.5% active ingredient solution suitable for many applications the tablet with a 20 mm diameter is dissolved in half litre water and the large tablet with the diameter of 50 mm (tab) in 10 litres of water. Both tablets can be dissolved in water within 25 to 45 seconds, accompanied by stirring. It is advantageous in the case of the larger tablet if, prior to introduction into the water or mixing with water, it is broken. This can also take place in the pack prior to opening.

EXAMPLE 2

The procedure of example 1 is repeated with the following mixture:

80 parts by weight chloramine-T 9 parts by weight cellulose powder 9 parts by weight corn starch (pregelatinized)

1 part by weight magnesium stearate 1 part by weight silicon dioxide (amorphous fumed silica)

The powder mixture obtained from these constituents can be pressed into tablets with adequate mechanical characteristics and good dissolving properties. Preferably, once again tablets with diameters of 20 and 50 mm are chosen. To have the same active ingredient quantity in a tablet as in example 1 in the case of the somewhat lower chloramine-T active ingredient content of 80%, the tablets are vertically slightly larger. With the smaller tablets pressing preferably takes place with a pressing force of 4 to 8 t. With the larger tablets (tabs) pressing preferably takes place with a pressing force of 20 t. Intermediate values of 8 to 20 t are also possible.

EXAMPLE 3

The procedure of example 1 is repeated with the following mixture:

90 parts by weight chloramine-T 1 part by weight highly disperse amorphous silicon dioxide (silica)

1.4 parts by weight high purity sodium carboxymethyl cellulose 1.5 parts by weight sodium carboxymethyl starch 0.8 part by weight high purity, microcrystalline cellulose 1.65 parts by weight Gum Arabic 0.2 part by weight magnesium stearate 2.1 parts by weight sodium chloride 0.05 part by weight dye 1.3 parts by weight perfume The mixture prepared from these constituents can be pressed to tablets having adequate mechanical characteristics and good dissolving properties. Preferably once again tablets with diameters of 20 and 50 mm are chosen and a tablet weight of 2.778 g is obtained for an active ingredient content of 2.5 g. Tablets without a polyethylene glycol content are particularly suitable for applications in environments with elevated temperatures of more than 30° C. In the same way the common salt serves to electrochemically stabilize the chloramine-T at higher temperatures and under non-optimum storage conditions. The addition of dye and perfume improve the appearance of the active ingredient tablet and makes their application more pleasant for the user.

What is claimed is:

1. Compressed tablets containing more than 80 wt. % of chloramine-T as the main constituent and at least one pressing agent and at least one agent assisting rapid dissolving as secondary constituents.

2. Tablets according to claim 1, wherein the chloramine-T content is at least 90 wt. %.

3. Tablets according to claim 1, wherein there is at least one secondary constituent, which acts both as a pressing agent and assists rapid dissolving.

4. Tablets according to claim 1, wherein the pressing agent is made of magnesium stearate, highly disperse amorphous silica, pulverulent polyethylene glycols, sodium carboxymethyl cellulose and/or microcrystalline cellulose.

5. Tablets according to claim 1, wherein the agent assisting rapid dissolving is made of sodium-starch glycolate, prepasted corn starch, sodium carboxymethyl cellulose and/or pulverulent polyethylene glycols.

6. Tablets according to claim 5, wherein said agent assisting rapid dissolving acts as a disintegrating agent.

7. Tablets according to claim 1, wherein the secondary constituents are water-soluble or at least sufficiently finely divided that a substantially clear solution is obtained on dissolving the tablets.

8. Tablets according to claim 1, wherein the tablets are constructed as dosing tablets and wherein the tablet size is adjusted in such a way that with predetermined liquid volumes it is possible to obtain solutions with a predetermined chloramine-T concentration.

9. Tablets according to claim 8, wherein said chloramine-T concentration is approximately 0.5 wt.

10. Tablets according to claim 1, wherein all the secondary constituents are biologically harmless.

11. Tablets according to claim 1, wherein at least the largest part of the secondary constituents is biodegradable.

12. Tablets according to claim 11, wherein all the secondary constituents are biodegradable.

13. Tablets according to claim 1, wherein said tablets can be dissolved in water, accompanied by stirring, within less than one minute.

14. Tablets according to claim 13, wherein said tablets can be dissolved in water within less than 45 seconds.

15. Tablets according to claim 1, wherein all the constituents are present at least in Deutsches Arzneibuch 10 Auflage (DAB 10) quality.

16. Tablets according to claim 1, herein said tablets are packed.

17. Tablets according to claim 16, wherein said tablets are packed in an airtight and moisture-tight form.

18. Tablets according to claim 16, wherein said tablets are packed sealed in polyethylene-coated soda kraft paper.

19. Tablets according to claim l, wherein said tablets have a density in the range of 1.00 $g/cm^3$ to 1.30 $g/cm^3$.

20. Tablets according to claim 19, wherein said tablets have a density of approximately 1.1 $g/cm^3$.

21. Method for producing tablets according to claim 1, wherein the starting substances are mixed dry in pulverulent form, the mixture is filled into a tablet press and pressed to tablets.

22. Method according to claim 21, wherein pressing takes place at pressures of 50 to 300 $N/mm^2$.

23. Method according to claim 22, wherein said pressures are 100 to 250 $N/mm^2$.

24. Method according to claim 21, with tablets having a diameter larger than 30 mm, the pressing pressure is adjusted in such a way that the tablets can still be broken by hand.

* * * * *

UNITED STATES PATENT AND TRADEMARK OFFICE
CERTIFICATE OF CORRECTION

PATENT NO. : 6,410,051 B1
DATED : June 25, 2002
INVENTOR(S) : Georg et al.

It is certified that error appears in the above-identified patent and that said Letters Patent is hereby corrected as shown below:

Column 2,
Line 4, "baths abattoirs," should read -- baths, abattoirs, --

Column 3,
Line 20, "6" should read -- 6 -- (no bold)
Line 65, "biogradable" should read -- biodegradable --

Column 4,
Line 2, "biogradable" should read -- biodegradable --

Column 5,
Line 1, "0.8 g/cm ." should read -- 0.8 g/cm$^3$. --

Column 6,
Line 33, "the-" should read -- the --
Line 44, "herein" should read -- wherein --
Line 62, "with" should read -- wherein with --

Signed and Sealed this

Thirty-first Day of December, 2002

JAMES E. ROGAN
*Director of the United States Patent and Trademark Office*